United States Patent
Mallard et al.

(10) Patent No.: US 8,859,603 B2
(45) Date of Patent: *Oct. 14, 2014

(54) METHOD FOR SOLUBILIZING METRONIDAZOLE

(75) Inventors: Claire Mallard, Mougins (FR); Alain Brzokewicz, Valbonne (FR)

(73) Assignee: Galderma S.A., Cham (CH)

( * ) Notice: Subject to any disclaimer, the term of this patent is extended or adjusted under 35 U.S.C. 154(b) by 381 days.

This patent is subject to a terminal disclaimer.

(21) Appl. No.: 13/110,116

(22) Filed: May 18, 2011

(65) Prior Publication Data

US 2011/0217357 A1 Sep. 8, 2011

Related U.S. Application Data

(63) Continuation of application No. 12/000,771, filed on Dec. 17, 2007, now Pat. No. 7,981,916, which is a continuation of application No. PCT/FR2006/001367, filed on Jun. 16, 2006.

(30) Foreign Application Priority Data

Jun. 17, 2004 (FR) ..................................... 05 06182

(51) Int. Cl.

| | | |
|---|---|---|
| *A61K 31/415* | (2006.01) | |
| *A61K 31/44* | (2006.01) | |
| *A61K 9/08* | (2006.01) | |
| *A61K 31/4164* | (2006.01) | |
| *A61K 47/10* | (2006.01) | |
| *A61K 47/22* | (2006.01) | |
| *A61K 9/00* | (2006.01) | |
| *A61K 9/06* | (2006.01) | |
| *A61K 9/12* | (2006.01) | |

(52) U.S. Cl.
CPC .................. *A61K 9/08* (2013.01); *A61K 31/415* (2013.01); *A61K 31/44* (2013.01); *A61K 9/0014* (2013.01); *A61K 9/06* (2013.01); *A61K 9/12* (2013.01); *A61K 9/122* (2013.01); *A61K 31/4164* (2013.01); *A61K 47/10* (2013.01); *A61K 47/22* (2013.01)
USPC .......................................... 514/398; 514/356

(58) Field of Classification Search
CPC ........................... A61K 31/415; A61K 31/44
USPC ................... 514/398, 356; 424/273; 260/309
See application file for complete search history.

(56) References Cited

U.S. PATENT DOCUMENTS

| | | |
|---|---|---|
| 4,032,645 A | 6/1977 | Chien et al. |
| 6,444,647 B1 | 9/2002 | Robinson et al. |
| 6,517,847 B2 | 2/2003 | Dow et al. |
| 7,981,916 B2 * | 7/2011 | Mallard et al. ................ 514/398 |
| 2004/0242463 A1 | 12/2004 | Kung et al. |

FOREIGN PATENT DOCUMENTS

| | | |
|---|---|---|
| JP | 58059913 | 4/2003 |
| WO | 0206349 A1 | 1/2002 |
| WO | 02094179 A2 | 11/2002 |
| WO | 03/057135 A2 | 7/2003 |

OTHER PUBLICATIONS

International Search Report corresponding to PCT/FR2006/001367, issued Dec. 1, 2006.
Chien, "Solubilization of Metronidazole by Water-Miscible Multi-Cosolvents and Water-Soluble Vitamins", Journal of Parenteral Science and Technology, Jan. 1984, vol. 38, No. 1, pp. 32-36.

* cited by examiner

*Primary Examiner* — Raymond Henley, III
(74) *Attorney, Agent, or Firm* — Dentons US LLP

(57) ABSTRACT

Metronidazole is solubilized in an aqueous phase, by mixing same with niacinamide and at least two glycolic cosolvents; the resulting solutions and pharmaceutical compositions comprised thereof are useful for the treatment of dermatological conditions/afflictions, notably rosacea.

21 Claims, No Drawings

US 8,859,603 B2

METHOD FOR SOLUBILIZING METRONIDAZOLE

CROSS-REFERENCE TO PRIOR EARLIER APPLICATIONS

This is a continuation of U.S. application Ser. No. 12/000,771, filed Dec. 17, 2007, now U.S. Pat. No. 7,981,916, which is a continuation of PCT/FR 2006/001367, filed Jun. 16, 2006 and designating the United States (published in the French language on Dec. 21, 2006 as WO 2006/134279 A2; the title and abstract were also published in English), which application claims foreign priority under 35 U.S.C. §119 of FR 05/06182, filed Jun. 17, 2005, each hereby expressly incorporated by reference in its entirety and each assigned to the assignee hereof.

BACKGROUND OF THE INVENTION

1. Technical Field of the Invention

The present invention relates to the formulation of bioactive ingredients for the purpose of pharmaceutical applications, in particular for topical application/administration.

The present invention relates, in particular, to a novel process for solubilizing metronidazole in a pharmaceutical composition, by combining, in an aqueous phase, at least metronidazole, niacinamide, propylene glycol and polyethylene glycol. Such combinations make it possible to solubilize the metronidazole therein.

This invention also relates to the solutions/compositions formulated via the subject solubilization process, to the method for preparing same, to the resulting compositions containing the metronidazole thus solubilized, and to the administration thereof in human or veterinary medicine.

2. Description of Background and/or Related and/or Prior Art

Metronidazole, or 1-(2-hydroxyethyl)-2-methyl-5-nitroimidazole, has long been known as a bioactive compound in the treatment of various conditions and afflictions, and in particular in the treatment of diseases due to various protozoa. When applied topically, metronidazole is also used in the treatment of various dermatological conditions, including rosacea (acne rosacae), bacterial ulcers and periorale dermatitis, as described in U.S. Pat. No. 4,837,378. Metronidazole also exhibits an anti-inflammatory activity when it is applied topically in the treatment of dermatological disorders, as described in U.S. Pat. No. 5,849,776. Metronidazole can also be used in the treatment of bacterial vaginosis, as an intravaginal therapeutic agent, as described in U.S. Pat. No. 5,536,743.

The compositions containing metronidazole for the treatment of dermatological disorders/afflictions are available in the form of a cream, a gel or a lotion. Noritate™ (Dermik Laboratories, Inc.) contains 1% of metronidazole dispersed in a white cream. Galderma Laboratories, Inc proposes MetroGel®, containing 0.75% by mass, relative to the total mass of the composition (m/m), of metronidazole solubilized in a transparent gel, MetroCream® containing 0.75% (m/m) of metronidazole solubilized in an emollient cream, and MetroLotion® containing 0.75% (m/m) of metronidazole solubilized in a lotion.

In the case of topical applications, products containing the active ingredient in solubilized form often exhibit better bioavailability than products in which the active ingredient is dispersed.

Given the low intrinsic solubility of metronidazole in an aqueous phase, which is on the order of 0.9% (m/m), the gelled aqueous compositions currently available on the market are limited to a concentration of 0.75% (m/m) of metronidazole, solubilized in the formulation. The metronidazole formulations in the form of creams have the advantage, over the gelled formulations currently available, of containing 1% (m/m) of metronidazole.

In general, the solubility of the active ingredients in an aqueous phase may be increased by including various non-ionic or ionic surfactants, lipid derivatives such as lecithins which allow the formation of lipid micelles, or cyclodextrins as often described in the literature.

Cyclodextrins make it possible to increase the water-solubility of various compounds. Cyclodextrins are in the form of a cage. The hydrophilic external part of this cage confers on them a certain solubility in aqueous media. Their inner part, which is more hydrophobic, allows the solubilization of amphiphilic or lipophilic molecules through the formation of inclusion complexes. The water-solubility of many molecules can therefore be substantially increased by employing these cyclodextrins. However, cyclodextrins have drawbacks in terms of cost, of limited solubility, of incompatibility with certain carriers or excipients, or of potential local or systemic toxicity. Furthermore, the formation of the inclusion complexes, complexation step, can be quite long, commonly several hours, and can affect the costs and processes for manufacturing the formulations.

Solubility-increasing agents other than cyclodextrins have been described. Yie W. Chien, *Journal of Parenteral Science and Technology*, 38 (1): 32-36 (January 1984), shows that the solubility of metronidazole in an aqueous solution can be increased by means of water-soluble vitamins such as niacinamide, pyridoxine hydrochloride and ascorbic acid. Chien subsequently describes that the water-solubility of metronidazole increases in a linear manner in relation to the concentration of these water-soluble vitamins in solution. In particular, Chien shows that it is necessary to have at least 9 mol of niacinamide in solution in order to solubilize 1 mol of metronidazole. In particular, Chien has shown that a combination of niacinamide with metronidazole in a molar ratio of 9 to 1 makes it possible to increase the solubility of metronidazole in an aqueous phase. Thus, in order to obtain a formulation containing 1% (m/m) of metronidazole solubilized in the aqueous phase, it is necessary to introduce a high niacinamide content on the order of 6.4% (m/m).

Y. Chang, G. Dow et al. describe in U.S. Pat. No. 6,468,989, on the basis of the studies by Chien et al., the use of cyclodextrins in combination with niacinamide in order to formulate gels containing 1% of metronidazole (m/m) with a niacinamide content below that of the prior art, i.e., only 1.25% (m/m). They have demonstrated a synergistic effect of the niacinamide/cyclodextrins combination on metronidazole solubility.

SUMMARY OF THE INVENTION

Surprisingly, it has now been found that metronidazole can be solubilized in the absence of the solvents conventionally described in the literature. More specifically, metronidazole has now been solubilized in the absence of cyclodextrin or of surfactant, and in the presence of a low niacinamide content.

The present invention thus features a novel process for solubilizing metronidazole in an aqueous phase. This invention therefore features a process for solubilizing metronidazole in a composition free of cyclodextrin or of surfactant and comprising a low niacinamide content.

The present invention also features aqueous solutions comprising metronidazole, niacinamide, at least two glycolic cosolvents, such as propylene glycol and a polyethylene glycol, and water.

In a third embodiment, the present invention features pharmaceutical compositions comprising the above solutions.

According to a fourth embodiment, a solution or a pharmaceutical composition according to the invention is administered as a medicament for the treatment of a dermatological condition, in particular rosacea, acne vulgaris or seborrhoeic dermatitis, and preferably rosacea.

DETAILED DESCRIPTION OF BEST MODE AND SPECIFIC/PREFERRED EMBODIMENTS OF THE INVENTION

The process according to the invention makes it possible to solubilize metronidazole in an aqueous phase at a concentration of greater than or equal to the concentration of 0.75% by mass relative to the total mass of the solution (m/m) usually present in commercialized formulations, and more particularly at a concentration of greater than or equal to 1% (m/m).

The process for solubilizing metronidazole according to the invention therefore comprises the step which entails mixing the metronidazole with niacinamide, in particular in a small amount, in an aqueous phase, along with glycolic solvent compounds, preferably at least two, in the absence of cyclodextrin and/or of surfactant.

The term "aqueous phase" means a phase composed predominantly of water.

The term "solubilization of metronidazole" means a dispersion in the molecular state in a liquid, no crystallization of the metronidazole being visible to the naked eye or even under a cross-polarization optical microscope.

According to the invention, the term "metronidazole" means metronidazole as such, but also in the form of a salt with a pharmaceutically acceptable acid, or else in the form of an ester. An exemplary salt is, in particular, metronidazole hydrochloride. The term "esters" means in particular metronidazole acetate, benzoate, myristate or monosuccinate.

According to the present invention, the niacinamide can be used as such, or else in the form of salts with a pharmaceutically acceptable acid.

Preferably, the niacinamide/metronidazole molar ratio employed in the process according to the invention is strictly less than 9, and preferably less than or equal to 5.5.

According to the present invention and, surprisingly, it has now effectively been demonstrated that the combination of 2 glycolic cosolvents in the presence of niacinamide makes it possible to increase the solubility of metronidazole in an aqueous phase.

Among the glycolic solvents according to the present invention, particularly exemplary are propylene glycol, butylene glycol, ethoxydiglycol, butoxydiglycol and polyethylene glycols (PEGs).

More particularly, the glycolic cosolvents are propylene glycol and at least one polyethylene glycol (PEG). The preferred PEGs are the liquid PEGs, such as PEGs 200; 300; 400; and 600.

Advantageously, a combination of 2 glycolic cosolvents is employed, which is a combination of propylene glycol with a polyethylene glycol (PEG). The preferred 2 cosolvents to be employed in combination according to the present invention are propylene glycol and PEG 400.

Indeed, as shown by the results presented in Examples 1 and 2 below, in the combination according to the invention, the propylene glycol, the PEG 400 and the niacinamide act in synergy to increase the aqueous solubility and the physical stability of the metronidazole solutions. In addition, the propylene glycol/PEG 400 combination makes it possible to considerably reduce the niacinamide/metronidazole molar ratio.

Preferably according to the present invention, this increase in solubility of metronidazole in an aqueous phase is obtained through the combination of 2 cosolvents, preferably propylene glycol/PEG 400, according to a ratio by mass of 1:1 in the presence of niacinamide. According to a preferred embodiment, the niacinamide/metronidazole molar ratio can be reduced to 4. According to an even more preferred embodiment, the combination according to the invention makes it possible to solubilize the metronidazole at least to a concentration of 1.56% (m/m), while at the same time having a niacinamide/metronidazole molar ratio strictly less than 9.

Advantageously, the process for solubilizing metronidazole according to the invention comprises, in particular, the following steps:

a) preparation of a solution of niacinamide, in particular at 10% (m/m) in water, until the niacinamide has completely dissolved. An amount of this solution is used, which amount depends, as previously indicated, on the amount of metronidazole to be dissolved and on the niacinamide/metronidazole molar ratio previously defined, b) introduction of the glycolic cosolvents, preferably two of them, into the solution obtained in a), c) after homogenization of the solution obtained in b), addition of a defined amount of metronidazole. This amount depends on the niacinamide/metronidazole molar ratio previously defined, d) after complete dissolution of the metronidazole, filtration of the solution obtained.

The metronidazole is then quantitatively determined in order to verify the percentage solubilized.

Preferably, the two cosolvents used for the solubilization according to the invention are propylene glycol and PEG 400.

Preferably, and in a manner that is in no manner limiting, the mixing is carried out by mechanical stirring, the filtration is carried out through a 1 µm filter and the metronidazole is quantitatively determined by measuring optical density by UV spectrophotometry at the wavelength of 327 nm.

Without cyclodextrin, the solubilization technique according to the invention is more advantageous since it does not require a complexation step.

Without surfactant necessary for the solubilization, the composition containing the metronidazole thus solubilized advantageously exhibits a reduced risk of skin irritations or skin allergies.

This invention also features the aqueous solutions of metronidazole that are obtained according to the process defined above.

The aqueous solutions according to the invention are characterized in that they comprise:
  metronidazole,
  niacinamide,
  at least 2 glycolic cosolvents, preferably 2, which are preferably propylene glycol and a polyethylene glycol,
  water.

Such solutions, comprising metronidazole in solubilized form, do not contain, in particular, any cyclodextrin.

In the solutions according to the invention, the metronidazole is present at a concentration of greater than or equal to 0.75% (m/m), preferably greater than or equal to 1% (m/m).

The niacinamide in the solutions according to the invention is present at a concentration such that the niacinamide/metronidazole molar ratio is strictly less than 9, preferably less than or equal to 5.5.

According to the invention, two glycolic cosolvents are preferably employed. The two glycolic cosolvents together, preferably propylene glycol and a polyethylene glycol, have a total concentration of between 2% and 50% (m/m), preferably between 5% and 20%, and more preferably equal to 10% (m/m), it being understood that they are present in a ratio by mass of 1:1. Preferably according to the invention, the propylene glycol and the polyethylene glycol are present in a ratio by mass of 1:1, each at the concentration of 5% (m/m).

Preferably, the solutions according to the invention have all the following properties:
metronidazole in a proportion greater than or equal to 1%,
niacinamide in a proportion such that the niacinamide/metronidazole molar ratio is strictly less than 9, and preferably less than or equal to 5.5,
propylene glycol and a polyethylene glycol in a ratio by mass of 1:1, the polyethylene glycol preferably being PEG 400.

The present invention also features pharmaceutical compositions comprising the above solutions. Such a composition comprises metronidazole in an amount of greater than or equal to 0.75% by weight relative to the total weight of the composition, preferably greater than or equal to 1% by weight relative to the total weight of the composition.

According to the present invention, the term "composition" means a pharmaceutical composition more particularly for use in the treatment of the skin and the mucous membranes, whether regime or regimen, and which can be in liquid, pasty or solid form, and more particularly in the form of salves, creams, milks, ointments, powders, impregnated pads, syndets, solutions, lotions, gels, sprays, foams, suspensions, sticks, shampoos or washing bases. Same can also be in the form of suspensions of microspheres or nanospheres or of lipid or polymeric vesicles or of polymeric or gelled patches for controlled release.

This invention also features the solutions and/or the compositions comprising the metronidazole thus solubilized, as medicaments.

More particularly, this invention thus features the formulation of the solutions and/or of the compositions comprising the metronidazole thus solubilized, into medicaments for the treatment of a dermatological condition, in particular rosacea, acne vulgaris or seborrhoeic dermatitis. Preferably, the dermatological condition is rosacea.

Finally, the present invention features the use of a combination of niacinamide and of at least two glycolic cosolvents, for solubilizing metronidazole in a composition comprising an aqueous phase substantially free of cyclodextrin.

The expression "aqueous phase substantially free of cyclodextrin" means an aqueous phase which does not contain cyclodextrin.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Preparation of Solutions

In this example, all the metronidazole solubility tests are carried out using a solution of niacinamide at 10% (m/m).

In the Case of Solutions Containing 1% (m/m) of Metronidazole without Cosolvent: (Solutions 1 to 3):
The metronidazole content is fixed at 1% (m/m).
According to the fixed niacinamide/metronidazole molar ratio, an amount of solution containing 10% of niacinamide is weighed out and is added to the amount of metronidazole previously weighed out, and then the mixture is made up to 100% through the addition of distilled water.
After magnetic stirring for 12 hours, the solution obtained is filtered through 1 μm and assayed by UV at the wavelength of 327 nm.

In the Case of Solutions Containing 1% (m/m) of Metronidazole with Cosolvent: (Solutions 4 to 6):
The metronidazole content is fixed at 1% (m/m) and the niacinamide/metronidazole molar ratio is fixed at 4.
Propylene glycol or PEG 400, alone or in combination, is/are added, as appropriate, to the amount of 10% (m/m) niacinamide solution corresponding to the molar ratio defined above. The metronidazole is then weighed out and added to the solution obtained. An amount of water is then added in order to make the mixture up to 100%.
After magnetic stirring for 12 hours, the solution obtained is filtered through 1 μm and assayed by UV at the wavelength of 327 nm.

In the Case of Solutions Saturated with Metronidazole: (Solutions 7 and 8):
The metronidazole content is fixed at 2% (m/m).
The propylene glycol and the PEG 400 are added, according to a ratio by mass of 1:1, to the amount of active ingredient previously weighed out. Depending on the case, the niacinamide in solution at 10% is added in such a way as to observe the niacinamide/metronidazole molar ratio of 4. A required amount of water is then added in order to make the mixture up to 100%.
After magnetic stirring for 12 hours, the solution obtained is filtered through 1 μm and assayed by UV at the wavelength of 327 nm.

The following solutions were therefore prepared:

TABLE 1

| Solutions | Composition | Content (% m/m) | Niacinamide/ metronidazole molar ratio | Measured concentration (% m/m) |
|---|---|---|---|---|
| No. 1 | Metronidazole | 1.0 | 10 | 1.016 |
| | Niacinamide 10% | 71.3 | | |
| | Distilled water | 27.7 | | |
| No. 2 | Metronidazole | 1.0 | 8 | 0.989 |
| | Niacinamide 10% | 57.0 | | |
| | Distilled water | 42.0 | | |
| No. 3 | Metronidazole | 1.0 | 4 | 1.023 |
| | Niacinamide 10% | 28.5 | | |
| | Distilled water | 70.5 | | |
| No. 4 | Metronidazole | 1.0 | 4 | 1.172 |
| | Niacinamide 10% | 28.5 | | |
| | PEG 400 | 5.0 | | |
| | Distilled water | 65.5 | | |
| No. 5 | Metronidazole | 1.0 | 4 | 1.185 |
| | Niacinamide 10% | 28.5 | | |
| | Propylene glycol | 5.0 | | |
| | Distilled water | 65.5 | | |
| No. 6 | Metronidazole | 1.0 | 4 | 1.03 |
| | Niacinamide 10% | 28.5 | | |
| | Propylene glycol | 5.0 | | |
| | PEG 400 | 5.0 | | |
| | Distilled water | 60.5 | | |
| No. 7 | Metronidazole | 2.0 | NA | 0.998 |
| | Propylene glycol | 5.0 | | |
| | PEG 400 | 5.0 | | |
| | Distilled water | 88.0 | | |

TABLE 1-continued

| Solutions | Composition | Content (% m/m) | Niacinamide/ metronidazole molar ratio | Measured concentration (% m/m) |
|---|---|---|---|---|
| No. 8 | Metronidazole | 2.0 | 4 | 1.565 |
| | Niacinamide 10% | 57.0 | | |
| | Propylene glycol | 5.0 | | |
| | PEG 400 | 5.0 | | |
| | Distilled water | 31.0 | | |

--: no data

Example 2

Stability Study

The solutions prepared according to Example 1 were monitored in terms of stability over a period of 8 weeks at ambient temperature and at +4° C. Since the latter condition is more drastic, it makes it possible to reveal more rapidly the potential metronidazole recrystallization phenomena.

The results obtained are the following:

TABLE II

| Solutions | Stability at +4° C. (visual observation) | Stability at ambient temperature (visual observation) |
|---|---|---|
| No. 1 | Clear | Clear |
| No. 2 | Precipitation at 13 days | Clear |
| No. 3 | Precipitation at 5 days | Clear |
| No. 4 | Precipitation at 8 days | Precipitation at 18 days |
| No. 5 | Precipitation at 8 days | Precipitation at 18 days |
| No. 6 | Clear | Clear |
| No. 7 | Precipitation at 8 days | Precipitation at 8 days |
| No. 8 | Clear | Clear |

Conclusions:

The comparison of solutions 1 and 2 made it possible to confirm the results of Chien et al., showing that it is necessary to introduce niacinamide into the aqueous solutions of metronidazole in order to increase its solubility and its physical stability in an aqueous phase. The niacinamide/metronidazole molar ratio should be greater than 8 in order to obtain a solution containing 1% (m/m) of metronidazole which is physically stable for 8 weeks at ambient temperature and at +4° C.

The comparison of solutions 3; 4; 5 and 6 shows that it is necessary to introduce the propylene glycol and the PEG 400 in combination according to a preferential ratio by mass of 1:1, in order to obtain a solution that is stable for 8 weeks at +4° C. and at ambient temperature. By virtue of this combination, the niacinamide/metronidazole molar ratio could be reduced to 4.

The comparison of solutions 7 and 8 shows the need to introduce niacinamide into the ternary mixture of water/propylene glycol/PEG 400 in order to obtain a solution that is stable over a period of 8 weeks at +4° C. and at ambient temperature.

The presence of the niacinamide in a solution saturated with metronidazole makes it possible to increase the solubility of the active ingredient at least up to 1.5% (m/m) without recrystallization (solution 8).

As a complement to the studies by Chien et al., this study also shows that the niacinamide/metronidazole molar ratio initially of 9 can be reduced by a factor of 2 in the presence of propylene glycol and PEG 400, preferably combined according to a ratio by mass of 1:1.

The results of this study therefore make it possible to envisage the formulation of metronidazole solubilized at 1% (m/m) with a niacinamide content of much less than 6.4 (m/m) without the use of cyclodextrins or of additional surfactants in the composition.

Example 3

Example of a Composition Containing Metronidazole at 1% (m/m)

a) Lotion at 1% (m/m):

| Ingredients | Formula (% m/m) |
|---|---|
| Metronidazole | 1.00 |
| Niacinamide | 2.85 |
| Propylene glycol | 5.00 |
| Macrogol 400 (PEG 400) | 5.00 |
| Benzyl alcohol | 1.30 |
| Glycerol | 5.00 |
| Stearyl alcohol | 2.00 |
| Mineral oil | 6.00 |
| Carbomer 981 NF | 0.15 |
| Arlacel 165 FL | 3.00 |
| Potassium sorbate | 0.20 |
| Cyclomethicone | 4.00 |
| Steareth 21 | 3.00 |
| 10% Sodium hydroxide | qs pH 5.0 ± 0.5 |
| Purified water | qs 100.00 |

The lotion is prepared according to the following procedure:

Aqueous Phase:

1) The water is weighed out into a beaker and the niacinamide, the Macrogol 400, the propylene glycol and the metronidazole are introduced with stirring using a deflocculator (300 rpm).

2) After complete dissolution of the metronidazole, the glycerol, the Carbomer 981 and the Steareth 21 are added.

3) The aqueous phase is heated to 70° C.

Fatty Phase:

1) The stearyl alcohol, the mineral oil and the Arlacel 165 FL are weighed out into a beaker.

2) The mixture is heated to 70° C. and stirred using a deflocculator (300 rpm).

Emulsification:

1) The fatty phase is gently introduced into the aqueous phase with vigorous stirring (900 rpm) using a stator rotor while maintaining the temperature at 70° C.

2) After introduction, the mixture is left to stir for 10 minutes.

3) The mixture is left to cool to ambient temperature with gentler stirring (300 rpm) and the cyclomethicone, the benzyl alcohol and the potassium sorbate are introduced.

4) The pH is adjusted with a 10% (m/m) sodium hydroxide solution if necessary.

5) The mixture is made up with water and homogenized if there has been evaporation of the water during emulsification.

b) Gel at 1% (m/m):

| Ingredients | Formula (% m/m) |
|---|---|
| Metronidazole | 1.00 |
| Niacinamide | 2.85 |
| Propylene glycol | 5.00 |
| Macrogol 400 (PEG 400) | 5.00 |
| Disodium edetate (EDTA) | 0.10 |

-continued

| Ingredients | Formula (% m/m) |
|---|---|
| Carbomer 980NF | 0.50 |
| Methyl para-hydroxybenzoate | 0.15 |
| Propyl para-hydroxybenzoate | 0.05 |
| 10% Sodium hydroxide | qs pH 5.0 ± 0.5 |
| Purified water | qs 100.00 |

The gel is prepared according to the following procedure:

1) The water is weighed out into a beaker and the niacinamide, the Macrogol 400, the propylene glycol and the metronidazole are introduced with stirring using a deflocculator (300 rpm).

2) After complete dissolution of the metronidazole, the Carbomer 980NF and the EDTA are added and the mixture is heated to 60° C. and homogenized using a deflocculator (600 rpm).

3) The mixture is left to cool to ambient temperature and the parabens are added, and the mixture is homogenized until complete dissolution is obtained (600 rpm).

4) The pH is adjusted using a 10% (m/m) sodium hydroxide solution if necessary.

5) The mixture is made up with water and homogenized if there has been evaporation.

c) Cream at 1% (m/m):

| Ingredients | Formula (% m/m) |
|---|---|
| Metronidazole | 1.00 |
| Niacinamide | 2.85 |
| Propylene glycol | 5.00 |
| Macrogol 400 (PEG 400) | 5.00 |
| Benzyl alcohol | 2.20 |
| Isopropyl myristate | 2.00 |
| Glycerol | 4.00 |
| Polawax NF | 12.50 |
| 90% Lactic acid | qs pH 5.0 ± 0.5 |
| Purified water | qs 100.00 |

The cream is prepared according to the following procedure:

Aqueous Phase:

1) The water is weighed out into a beaker and the niacinamide, the Macrogol 400, the propylene glycol and the metronidazole are introduced with stirring using a deflocculator (300 rpm).

2) After complete dissolution of the metronidazole, the glycerol is added.

3) The aqueous phase is heated to 70° C.

Fatty Phase:

1) The isopropyl myristate and the Polawax NF are weighed out into a beaker.

2) The mixture is heated to 70° C. and stirred using a deflocculator (300 rpm).

Emulsification:

1) The fatty phase is gently introduced into the aqueous phase with vigorous stirring (900 rpm) using a stator rotor while maintaining the temperature at 70° C.

2) After introduction, the mixture is left to stir for 10 minutes.

3) The mixture is left to cool to ambient temperature with gentler stirring (300 rpm) and the benzyl alcohol is introduced.

4) The pH is adjusted with a 90% lactic acid solution if necessary.

5) The mixture is completed with water and homogenized if there has been evaporation of water during the emulsification.

d) Spray at 1% (m/m):

| Ingredients | Formula (% m/m) |
|---|---|
| Metronidazole | 1.00 |
| Niacinamide | 2.85 |
| Propylene glycol | 5.00 |
| Macrogol 400 (PEG 400) | 5.00 |
| Xanthan gum | 1.00 |
| Benzyl alcohol | 2.00 |
| Ethanol | 30.00 |
| Purified water | qs 100.00 |

The spray is prepared according to the following procedure:

1) The water is weighed out into a beaker and the niacinamide, the Macrogol 400, the propylene glycol and the metronidazole are introduced with stirring using a deflocculator (300 rpm).

2) After complete dissolution of the metronidazole, the xanthan gum is added and the mixture is heated to 60° C. and left to homogenize (600 rpm).

3) After complete dissolution of the xanthan gum, the mixture is left to cool to ambient temperature and the ethanol and the benzyl alcohol are added.

4) The mixture is homogenized until a clear solution is obtained (300 rpm).

Example 4

Examples of Compositions Containing Metronidazole at Concentrations Greater than 1% (m/m)

a) Gel at 1.5% (m/m):

| Ingredients | Formula (% m/m) |
|---|---|
| Metronidazole | 1.50 |
| Niacinamide | 5.70 |
| Propylene glycol | 5.00 |
| Macrogol 400 (PEG 400) | 5.00 |
| Disodium edetate (EDTA) | 0.10 |
| Carbomer 940 | 0.60 |
| Methyl para-hydroxybenzoate | 0.15 |
| Propyl para-hydroxybenzoate | 0.05 |
| 10% Sodium hydroxide | qs pH 5.0 ± 0.5 |
| Purified water | qs 100.00 |

The gel at 1.5% (m/m) is prepared according to the same protocol as the gel at 1% (m/m).

b) Foam at 1.5% (m/m):

| Ingredients | Formula (% m/m) |
|---|---|
| Metronidazole | 1.50 |
| Niacinamide | 5.70 |
| Propylene glycol | 5.00 |
| Macrogol 400 (PEG 400) | 5.00 |
| Methylcellulose | 0.30 |
| Xanthan gum | 0.30 |
| PEG-40 stearate | 3.00 |
| Polysorbate 80 | 1.00 |
| Glyceryl monostearate | 0.50 |
| Methylparaben | 0.15 |

-continued

| Ingredients | Formula (% m/m) |
|---|---|
| Propylparaben | 0.05 |
| Phenoxyethanol | 1.00 |
| Mineral oil | 6.00 |
| Stearic acid | 1.00 |
| Miglyol | 6.00 |
| Purified water | 55.7 |
| Propellant gas | qs |
| | 100.00 |

The foam is prepared according to the following procedure:

Aqueous Phase:

1) The water is weighed out into a beaker and the niacinamide, the Macrogol 400, the propylene glycol and the metronidazole are introduced with stirring using a deflocculator (300 rpm).

2) After complete dissolution of the metronidazole, the aqueous phase is heated to 70° C. and the xanthan gum, the methylcellulose, the PEG-40 stearate, the polysorbate 80 and the glyceryl monostearate are added.

3) The methyl paraben is added while maintaining the temperature and the stirring.

Fatty Phase:

1) The stearic acid and the mineral oil are weighed out into a beaker.

2) The mixture is allowed to melt in a water bath at 70° C. and then homogenized while maintaining the stirring.

Emulsification:

1) The fatty phase is introduced gently into the aqueous phase with vigorous stirring (900 rpm) using a stator rotor while maintaining the temperature at 70° C.

2) The mixture is allowed to cool to ambient temperature with gentler stirring (300 rpm) to a temperature below 50° C.

3) The phenoxyethanol is added and the mixture is allowed to cool to ambient temperature with gentle stirring.

4) The mixture is made up with water and homogenized if there has been evaporation of water during the emulsification.

Packaging:

The oil-in-water emulsion thus obtained is introduced into an aerosol packaging. After the container has been sealed, the propellant gas is introduced.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for solubilizing metronidazole, comprising admixing, in an aqueous phase, said metronidazole with niacinamide or salt thereof and at least two glycolic cosolvents, in the absence of cyclodextrin.

2. The solubilization process as defined by claim 1, wherein the proportion of metronidazole, by mass relative to the total mass of the resulting solution, is greater than or equal to 0.75%.

3. The solubilization process as defined by claim 2, wherein the proportion of metronidazole, by mass relative to the total mass of the resulting solution, is greater than or equal to 1%.

4. The solubilization process as defined by claim 1, wherein the niacinamide/metronidazole molar ratio is less than 9.

5. The solubilization process as defined by claim 4, wherein the niacinamide/metronidazole molar ratio is less than or equal to 5.5.

6. The solubilization process as defined by claim 1, said glycolic cosolvents comprising propylene glycol and at least one polyethylene glycol.

7. The solubilization process as defined by claim 6, said at least one polyethylene glycol comprising PEG 400.

8. The solubilization process as defined by claim 1, wherein two glycolic cosolvents are admixed.

9. The solubilization process as defined by claim 8, wherein said glycolic cosolvents are present in a ratio by mass of 1:1.

10. The solubilization process as defined by claim 1, which comprises the following steps:
    a) preparing a solution of niacinamide in water, until complete dissolution of the niacinamide is attained,
    b) introducing the glycolic cosolvents into the solution obtained in a),
    c) homogenizing the solution obtained in b), and then adding a defined amount of metronidazole,
    d) after complete dissolution of the metronidazole, filtering the solution obtained.

11. An aqueous solution of metronidazole, prepared according to the process as defined by claim 1.

12. An aqueous solution comprising metronidazole, niacinamide or salt thereof and at least two glycolic cosolvents.

13. The aqueous solution as defined by claim 12, devoid of cyclodextrin.

14. The aqueous solution as defined by claim 12, which comprises:
    1) metronidazole in a proportion of greater than or equal to 1%,
    2) niacinamide in a proportion such that the niacinamide/metronidazole molar ratio is less than 9,
    3) propylene glycol and at least one polyethylene glycol in a ratio by mass of about 1.1.

15. The aqueous solution as defined by claim 14, wherein the niacinamide/metronidazole molar ratio is less than or equal to 5.5.

16. The aqueous solution as defined by claim 15, which comprises propylene glycol and polyethylene glycol 400.

17. A pharmaceutical composition which comprises the aqueous solution as defined by claim 12.

18. A regime or regimen for the treatment of a dermatological condition/affliction, comprising administering to a subject in need of such treatment, a thus effective amount of a pharmaceutical composition as defined by claim 17.

19. A regime or regimen for the treatment of rosacea, comprising topically applying onto the affected skin area of a subject in need of such treatment, a thus effective amount of a pharmaceutical composition as defined by claim 17.

20. The regime or regimen as defined by claim 19, said pharmaceutical composition being devoid of cyclodextrin.

21. The pharmaceutical composition as defined by claim 17, formulated as a salve, cream, milk, ointment, powder, impregnated pad, syndet, lotion, gel, spray, foam, suspension, stick, shampoo, washing base, microspheres, nanospheres, vesicles, or a controlled release patch.

* * * * *

UNITED STATES PATENT AND TRADEMARK OFFICE
CERTIFICATE OF CORRECTION

| | | |
|---|---|---|
| PATENT NO. | : 8,859,603 B2 | Page 1 of 1 |
| APPLICATION NO. | : 13/110116 | |
| DATED | : October 14, 2014 | |
| INVENTOR(S) | : Mallard et al. | |

It is certified that error appears in the above-identified patent and that said Letters Patent is hereby corrected as shown below:

On the Title page, Item [30], should read "Jun. 17, 2005"

Signed and Sealed this
Third Day of March, 2015

Michelle K. Lee
*Deputy Director of the United States Patent and Trademark Office*